US00PP25051P3

(12) United States Plant Patent
Suphachadiwong

(10) Patent No.: US PP25,051 P3
(45) Date of Patent: Nov. 11, 2014

(54) *PHALAENOPSIS* PLANT NAMED 'SUPHAL1301'

(50) Latin Name: ***Phalaenopsis* hybrid**
Varietal Denomination: SUPHAL1301

(71) Applicant: Thumrong Suphachadiwong, Chonburi (TH)

(72) Inventor: Thumrong Suphachadiwong, Chonburi (TH)

(73) Assignee: Suphachatawong Innovation (TH)

( * ) Notice: Subject to any disclaimer, the term of this patent is extended or adjusted under 35 U.S.C. 154(b) by 34 days.

(21) Appl. No.: 13/815,809

(22) Filed: Mar. 15, 2013

(65) Prior Publication Data

US 2014/0283261 P1 Sep. 18, 2014

(51) Int. Cl.
*A01H 5/00* (2006.01)

(52) U.S. Cl.
USPC ..... Plt./311

(58) Field of Classification Search
USPC ..... Plt./311
See application file for complete search history.

*Primary Examiner* — Kent L Bell

(74) *Attorney, Agent, or Firm* — Cassandra Bright

(57) ABSTRACT

A new and distinct *Phalaenopsis* cultivar named 'SUPHAL1301' is disclosed, characterized by very distinctive deep Greyed-Purple and brown flower color, small plant size and dark stems. The new variety is a *Phalaenopsis*, typically produced as an indoor ornamental plant.

2 Drawing Sheets

Figure 1:
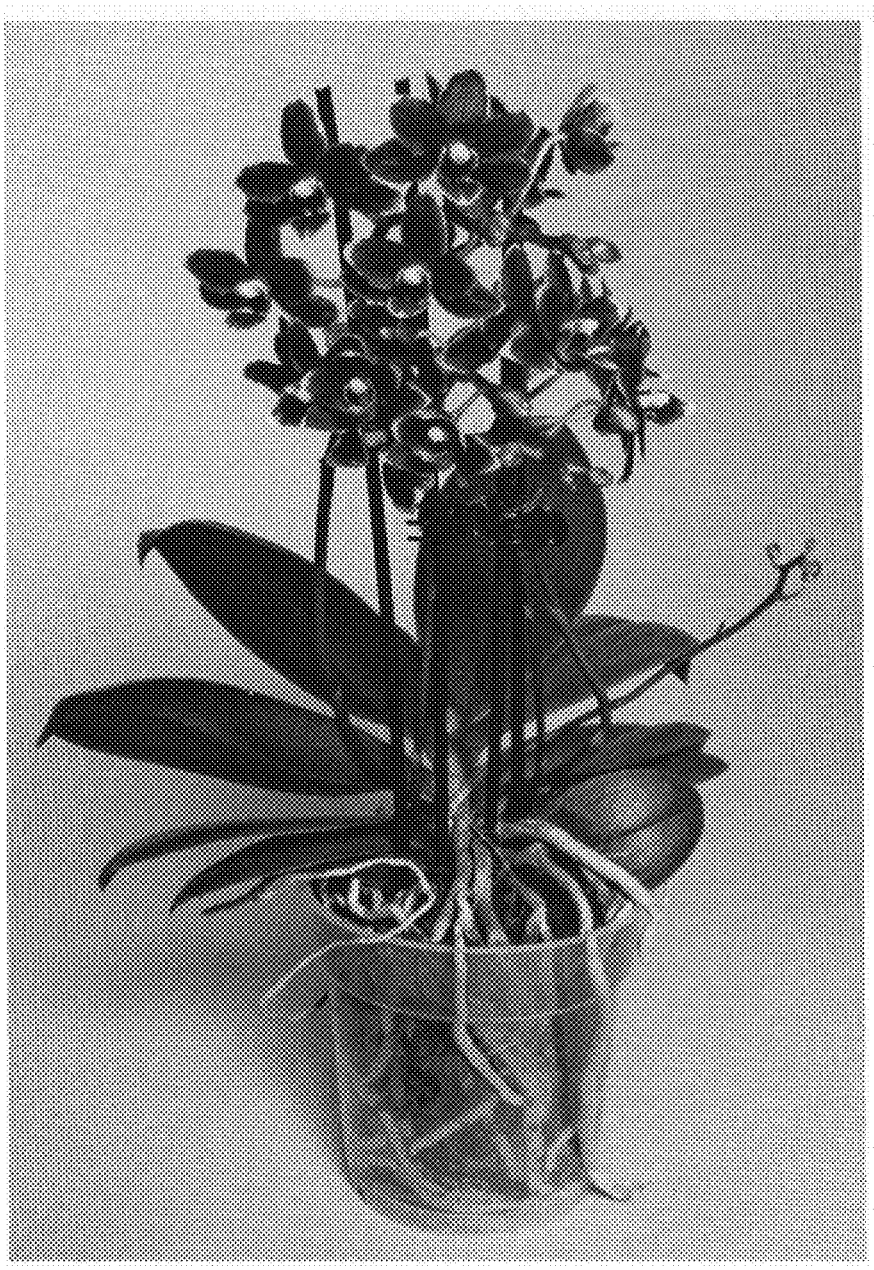

Latin name of the genus and species: *Phalaenopsis* hybrid. Variety denomination: 'SUPHAL1301'.

BACKGROUND OF THE INVENTION

This application relates to a new cultivar of *Phalaenopsis* hybrid. The new variety is the product of a planned breeding program. The new variety originated as a seedling from the crossing of the unpatented, proprietary seed parent *Phalaenopsis* 'TB637' with the unpatented, proprietary pollen parent referred to as *Phalaenopsis* 'TB642'. The crossing was made by the inventor in his research greenhouse in Chonburi, Thailand in March of 2006.

The new variety was first selected by the inventor, Thumrong Suphachadiwong, a citizen of Thailand, in July of 2009 in a research greenhouse belonging to the inventor in Chonburi, Thailand. After identifying the new variety as a potentially interesting selection, the inventor continued confidential testing and propagation of 'SUPHAL1301', assessing stability of the unique characteristics of this variety.

Asexual reproduction of the new cultivar 'SUPHAL1301' was first performed at a commercial laboratory belonging to the inventor in Chonburi, Thailand by tissue culture in August of 2009. Access to all plants was restricted, as plants were kept in a greenhouse not open to the public, and tissue culture plantlets were in a laboratory belonging to the inventor, and not accessible to the public. Through subsequent propagation, multiple generations have been reproduced, which have shown that the unique features of this cultivar are stable and reproduced true to type.

SUMMARY OF THE INVENTION

The cultivar 'SUPHAL1301' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SUPHAL1301'. These characteristics in combination distinguish 'SUPHAL1301' as a new and distinct *Phalaenopsis* cultivar:

1. Very distinctive deep greyed-purple and brown flower color.
2. Small plant size.
3. Unique dark peduncles.

PARENT COMPARISON

Plants of the new cultivar 'SUPHAL1301' are similar to the seed parent, *Phalaenopsis* 'TB637' in most horticultural characteristics. The new variety, however, produces a darker flower color than the seed parent.

Plants of the new cultivar 'SUPHAL1301' are similar to the pollen parent, *Phalaenopsis* 'TB642' in most horticultural characteristics. Plants of the new variety however, are more compact plant with darker colored leaves than the pollen parent.

COMMERCIAL COMPARISON

'SUPHAL1301' is similar to the unpatented commercial variety *Phalaenopsis* 'Zaragoza' in most horticultural characteristics. However the new variety, 'SUPHAL1301' has a much smaller flower and leaf size as well as a shorter plant height than comparator 'Zaragoza'. Additionally the new variety 'SUPHAL1301' produces a lip, sepal, petal, and side lobe of different shape than those of comparator 'Zaragoza'. Also the new variety 'SUPHAL1301' produces a flower of darker coloration and leaves of different angle than those of comparator 'Zaragoza'.

BRIEF DESCRIPTION OF THE PHOTOGRAPHS

The accompanying photograph in FIG. 1 illustrates in full color a typical plant of 'SUPHAL1301' grown in a commercial greenhouse in Zuidbroek, the Netherlands. This plant is approximately 18 months old after deflasking, shown planted in an 11 cm container.

Figure 2:
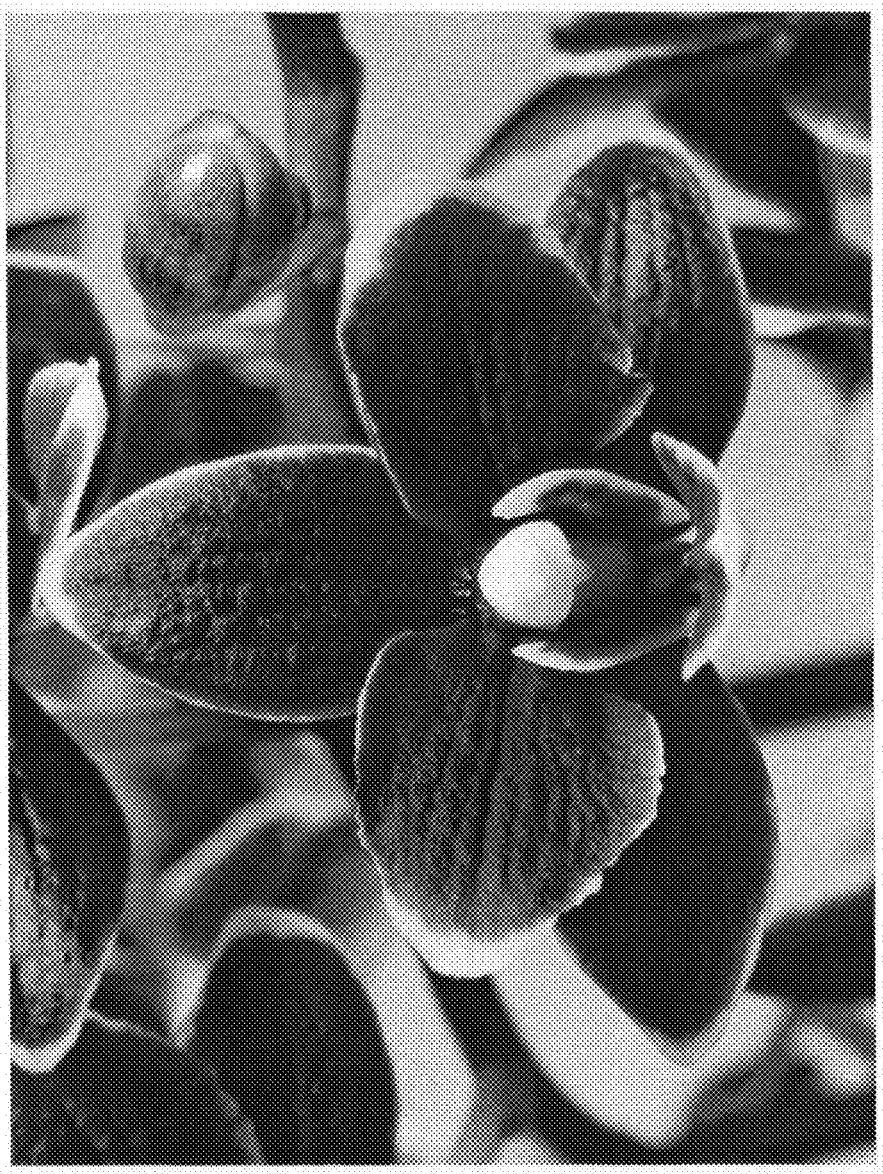

FIG. 2 illustrates a close up of the individual flower. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'SUPHAL1301' plants grown in a greenhouse in Zuidbroek, the Netherlands. Temperatures ranged between 18° C. and 28° C. day and night. No photoperiodic or chemical treatments were given to the plants. During bright Summer conditions, shade was given. During dark Winter months, supplemental light was given at unspecified amounts. Measurements and numerical values represent averages of typical plant types.

Botanical classification: *Phalaenopsis* hybrid 'SUPHAL1301'.

PROPAGATION

Type of propagation typically used: Tissue culture.

Time to initiate roots: About 21 days at approximately 28° C.

Time to produce a rooted cutting/liner: About 26 weeks at approximately 18° C. to 28° C.

Root description: Thick (typical for *Phalaenopsis*) and rounded, average diameter: 5 mm, colored greyed-green; near RHS 191A and 191C.

PLANT

Growth habit: Monopodial.

Height from top of soil line to top of foliage: Average 14.2 cm.

Height from top of soil line to top of flowers: Average 25.1 cm.

Plant spread: At widest, average: 28.5 cm; at narrowest: 20.5 cm.

Normal pot size: 11 cm.

Growth rate: Moderate.

Number of leaves per plant: Average 8.

FOLIAGE

Leaf:

- *Arrangement*.—Distichous.
- *Average length*.—Approximately 12.6 cm (including sheath).
- *Average width*.—Approximately 7.0 cm.
- *Shape of blade*.—Elliptic to obovate.
- *Aspect*.—Horizontal to slightly upward.
- *Apex*.—Unequal acute, with a mucronate tip; tip pointed downward.
- *Base*.—Cuneate. Sheath length: Average 1.2 cm. Sheath width: Average 1.1 cm. Sheath color: Yellow-green; near RHS 146C to 146D.
- *Margin*.—Entire.
- *Texture of top surface*.—Smooth, moderately furrowed.
- *Texture of bottom surface*.—Smooth.
- *Appearance of top surface*.—Moderately glossy.
- *Appearance of bottom surface*.—Very slightly glossy.
- *Color*.—Young foliage upper side: Green to yellow-green; in between near RHS 143A and 146A but darker. Young foliage under side: Yellow-green; near RHS 147A, heavily tinged brown; near RHS N200B. Mature foliage upper side: Green; near RHS N137B. Mature foliage under side: Yellow-green; near RHS 146B, margins heavily tinged brown; near RHS 200B.

Venation:

- *Type*.—Camptodromous.
- *Venation coloration*.—Upper side: Green; near RHS N137B, main vein yellow-green; near RHS 147A. Under side: Yellow-green; near RHS 146B, main vein on under side green; near RHS 143A, tinged brown towards the tip; near RHS 200B.

Petiole: No petiole present.

FLOWERING CHARACTERISTICS

Flower bud:

- *Rate of opening*.—Fully open approximately five days after stage described.
- *Length*.—Approximately 1.2 cm.
- *Diameter*.—Approximately 0.8 cm wide and 1.0 cm high.
- *Shape*.—Broad ovate.
- *Color*.—Yellow-green; near RHS 144B and 144C, heavily tinged greyed-purple to brown; in between near RHS N186C and 200A, heavier tinge towards the base.

Peduncle:

- *Length*.—Approximately 22.8 cm.
- *Width*.—Approximately 0.3 cm.
- *Aspect*.—Approximately 45° angle to rosette.
- *Strength*.—Strong
- *Texture*.—Smooth.
- *Appearance*.—Moderately glossy.
- *Color*.—Yellow-green to brown; in between near RHS 147A and N200A, finely dotted yellow-green; near RHS 145D.

Inflorescence:

- *Flowers per stem*.—Average 11.
- *Inflorescence arrangement*.—Compound panicle.
- *Inflorescence height*.—Approximately 9.6 cm (measured from lowest branching of panicle to top of inflorescence).
- *Inflorescence width*.—Approximately 10.5 cm.

Individual flowers:

- *Flower type*.—Single zygomorphic flower.
- *Shape*.—Rounded deltate.
- *Length* (*height*).—Approximately 3.2 cm.
- *Width*.—Approximately 4.3 cm.
- *Depth*.—Approximately 2.0 cm.
- *Fragrance*.—No fragrance.
- *Persistent*.—Non-persistent.
- *Quantity of petals*.—2 true petals.

Petals:

- *Arrangement*.—One petal on each side of the column.
- *Length*.—Approximately 1.8 cm.
- *Width*.—Approximately 1.3 cm.
- *Shape*.—Ovate.

*Apex*.—Broad acute.
*Base*.—Broad cuneate.
*Margin*.—Irregular finely angulate.
*Texture*.—Upper (forward) surface: Smooth, slightly velvety.
*Texture*.—Lower (back) surface: Smooth, slightly velvety.
*Appearance*.—Slightly glossy all surfaces. Color: When opening, forward surface: Brown; near RHS 200A, tinged greyed-purple; near RHS 187B, especially towards the margins, tip yellow-green; 154C to 154D. When opening, back surface: Greyed-purple; near RHS N187B to N187C, margins more purplish; in between near RHS 187A and 187B, tip yellow-green; 154C to 154D. Fully Opened, forward surface: Greyed-purple; near RHS 187A, lighter towards the margins; near RHS 187B, tip yellow-green and white; 154D and 155A. Fully Opened, back surface: Greyed-purple to purple; in between near RHS N187C and 76A, margins greyed-purple; near RHS 187B, tip yellow-green; 154D. Fading, forward surface: Not fading. Fading, back surface: Not fading.
*Color venation*.—Fully Opened, forward surface: No venation visible other than petal color. Fully Opened, back surface: No venation visible other than petal color.

Labellum:
*Shape*.—Three-parted.
*Length*.—Approximately 1.9 cm.
*Width*.—Approximately 1.1 cm.
*Texture*.—Smooth, slightly velvety.
*Appearance*.—Very slightly glossy.
*Tip*.—Obtuse.
*Base*.—Cuneate.
*Color*.—When opening, forward surface: Central lobe greyed-purple; near RHS 187A, lighter towards the margins; near RHS 187D, outer margin white; near RHS NN155C to NN155D, tip green-yellow; near RHS 1D, base green-yellow; near RHS 1B to 1C, lateral lobes brown; near RHS 200A, tinged greyed-purple; near RHS 187B, especially towards the margins, tip white; near RHS NN155C to NN155D, callosities greyed-purple; near RHS N186C. When opening, back surface: Central lobe greyed-purple to purple; in between near RHS N187C and 76A, tip white; near RHS 155A base yellow-green; near RHS 154D, lateral lobes greyed-purple; near RHS N186C, tip white; near RHS NN155C to NN155D. Fully Opened, forward surface: Central lobe greyed-purple; near RHS 187A, lighter towards the margins; near RHS 187D, tip and outer margin white; near RHS NN155C to NN155D, base green- yellow; near RHS 1B to 1C, lateral lobes brown; near RHS 200A, tinged greyed-purple; near RHS 187B, especially towards the margins, tip white; near RHS NN155C to NN155D, callosities greyed-purple; near RHS N186C. Fully Opened, back surface: Central lobe greyed-purple to purple; in between near RHS N187C and 76A, tip white; near RHS 155A base yellow-green; near RHS 154D, lateral lobes greyed-purple; near RHS N186C, tip white; near RHS NN155C to NN155D. Fading, forward surface: Not fading, only change is the texture becomes non-velvety. Fading, back surface: Not fading, only change is the texture becomes non-velvety. Color Venation Fully Opened, forward surface: No venation visible. Fully Opened, back surface: No venation visible. Margin: Entire.

Sepals:
*Quantity*.—3.
*Length*.—Approximately 2.1 cm.
*Width*.—Approximately 1.2 cm.
*Shape*.—Ovate.
*Apex*.—Broad bluntly acute to obtuse.
*Base*.—Broad cuneate.
*Margin*.—Entire.
*Texture*.—Smooth, slightly velvety all surfaces.
*Appearance*.—Very slightly glossy, all surfaces.
*Color*.—Fully Opened, forward surface: Greyed-purple; near RHS N186C, lighter towards the margin; near RHS 187A, 187B and 187C, tip yellow-green; 154C to 154D. Fully Opened, back surface: Yellow-green; near RHS 152D, base greyed-purple; near RHS N186C.

Pedicels:
*Length*.—Approximately 3.1 cm.
*Diameter*.—Approximately 0.2 cm.
*Angle*.—Approximately 85° to peduncle.
*Strength*.—Moderately strong.
*Texture*.—Smooth.
*Appearance*.—Moderately glossy.
*Color*.—Yellow-green; near RHS 150D, more green towards base; near RHS 146C.

REPRODUCTIVE ORGANS

Stamens, style and stigma fused into column: Yes.
Column length: Approximately 0.8 cm.
Column diameter: Approximately 0.4 cm.
Column color: White; near RHS NN155D, with a small Purple dot on each side; near RHS 77B.
Ovary:
*Position*.—Inferior.
*Diameter*.—Approximately 0.3 cm.
*Color*.—White; near RHS NN155D.
Pollen color: Yellow-orange; near RHS 21A.

OTHER CHARACTERISTICS

Disease resistance: Neither resistance nor susceptibility to the normal diseases found in *Phalaenopsis* has been observed.
Drought tolerance and cold tolerance: Normal for species.
Fruit/seed production: No fruits/seeds detected to date.

What is claimed is:

1. A new and distinct cultivar of *Phalaenopsis* plant named 'SUPHAL1301' as herein illustrated and described.

* * * * *